United States Patent
Qadir et al.

(10) Patent No.: US 12,327,399 B2
(45) Date of Patent: Jun. 10, 2025

(54) CO-TRAINING FRAMEWORK TO MUTUALLY IMPROVE CONCEPT EXTRACTION FROM CLINICAL NOTES AND MEDICAL IMAGE CLASSIFICATION

(71) Applicant: KONINKLIJKE PHILIPS N.V., Eindhoven (NL)

(72) Inventors: Ashequl Qadir, Melrose, MA (US); Kathy Mi Young Lee, Westford, MA (US); Claire Yunzhu Zhao, Boston, MA (US); Minnan Xu, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 373 days.

(21) Appl. No.: 17/781,081

(22) PCT Filed: Dec. 16, 2020

(86) PCT No.: PCT/EP2020/086320
§ 371 (c)(1),
(2) Date: May 31, 2022

(87) PCT Pub. No.: WO2021/122670
PCT Pub. Date: Jun. 24, 2021

(65) Prior Publication Data
US 2023/0005252 A1 Jan. 5, 2023

Related U.S. Application Data

(60) Provisional application No. 62/949,836, filed on Dec. 18, 2019.

(51) Int. Cl.
*G06V 10/774* (2022.01)
*G06F 40/279* (2020.01)
(Continued)

(52) U.S. Cl.
CPC ........ *G06V 10/7753* (2022.01); *G06F 40/279* (2020.01); *G06V 10/764* (2022.01);
(Continued)

(58) Field of Classification Search
CPC ........... G06V 10/7753; G06V 10/7747; G06V 20/70; G06V 10/776; G06V 10/764;
(Continued)

(56) References Cited

U.S. PATENT DOCUMENTS

| | | | | |
|---|---|---|---|---|
| 11,720,621 B2 * | 8/2023 | Lombardo | ............ | G06F 16/906 715/700 |
| 11,943,364 B2 * | 3/2024 | Streit | .................. | G06F 21/6245 |

(Continued)

FOREIGN PATENT DOCUMENTS

| | | |
|---|---|---|
| WO | WO2018094296 A1 | 5/2018 |
| WO | WO2019160557 A1 | 8/2019 |

OTHER PUBLICATIONS

PCT International Search Report, International application No. PCT/EP2020/086320, Apr. 15, 2021.

(Continued)

*Primary Examiner* — John J Lee

(57) ABSTRACT

A system and method for training a text report identification machine learning model and an image identification machine learning model, including: initially training a text report machine learning model, using a labeled set of text reports including text pre-processing the text report and extracting features from the pre-processed text report, wherein the extracted features are input into the text report machine learning model; initially training an image machine learning model, using a labeled set of images; applying the initially trained text report machine learning model to a first set of unlabeled text reports with associated images to label the associated images; selecting a first portion of labeled (Continued)

associated images; re-training the image machine learning model using the selected first portion of labeled associated images; applying the initially trained image machine learning model to a first set of unlabeled images with associated text reports to label the associated text reports; selecting a first portion of labeled associated text reports; and re-training the text report machine learning model using the selected first portion of labeled associated text reports.

20 Claims, 6 Drawing Sheets

(51) Int. Cl.
  *G06V 10/764* (2022.01)
  *G06V 10/776* (2022.01)
  *G06V 20/70* (2022.01)
  *G16H 15/00* (2018.01)
  *G16H 30/20* (2018.01)
(52) U.S. Cl.
  CPC ........ *G06V 10/7747* (2022.01); *G06V 10/776* (2022.01); *G06V 20/70* (2022.01); *G16H 15/00* (2018.01); *G16H 30/20* (2018.01); *G06V 2201/03* (2022.01)
(58) Field of Classification Search
  CPC .. G06V 2201/03; G06V 10/774; G16H 15/00; G16H 30/20; G06F 40/279
  See application file for complete search history.

(56) References Cited

U.S. PATENT DOCUMENTS

| | | |
|---|---|---|
| 2019/0188848 A1 | 6/2019 | Madani |
| 2021/0065859 A1* | 3/2021 | McKinney ............. G16H 30/40 |
| 2021/0295503 A1* | 9/2021 | Amundson ........... G06T 7/0014 |

OTHER PUBLICATIONS

Haug P.J. et al., "Computerized Extraction of Coded Findings from Free-Text Radiologic Reports. Work in Progress", vol. 174, issue 2, pp. 543-548, Feb. 1990. https://pubs.rsna.org/doi/abs/10.1148/radiology.174.2.2404321.

Cornegruta S. et al., "Modelling Radiological Language with Bidirectional Long Short-Term Memory Networks", arXiv preprint arXiv:1609.08409 (2016).

Huang Z. et al., "Bidirectional LSTM-CRF Models for Sequence Tagging", arXiv preprint arXiv:1508.01991, 2015.

Blum A. et al., "Combining Labeled and Unlabeled Data with Co-Training", COLT' 98: Proceedings of the Eleventh Annual Conference on Computational Learning Theory, pp. 92-100, Jul. 1998.

Selvaraju R.R. et al., "Grad-CAM: Why Did You Say That? Visual Explanations from Deep Networks via Gradient-based Localization", NIPS 2016 Workshop on Interpretable Machine Learning in Complex Systems, Computer Vision and Pattern Recognition (cs.CV); Machine Learning (cs.LG), 2016.

Prasad M. et al., "Multi-View Learning for Bronchovascular Pair Detection", Proceedings of the 2004 Intelligent Sensors, Sensor Networks and Information Processing Conference, pp. 587-592, 2004.

Gao Z. et al., "HEp-2 Cell Classification with Deep Convolutional Neural Networks", IEEE Journal of Biomedical and Health Informatics, vol. 21, issue 2, pp. 416-428, 2015.

Rvin J. et al., "CheXpert: A Large Chest Radiograph Dataset with Uncertainty Labels and Expert Comparison", Proceedings of the AAAI Conference on Artificial Intelligence, vol. 33, No. 01, 2019.

Moradi M. et al., "A Hybrid Learning Approach for Semantic Labeling of Cardiac CT Slices and Recognition of Body Position", 2016 IEEE 13th International Symposium on Biomedical Imaging (ISBI), pp. 1418-1421, 2016.

* cited by examiner

CO-TRAINING FRAMEWORK TO MUTUALLY IMPROVE CONCEPT EXTRACTION FROM CLINICAL NOTES AND MEDICAL IMAGE CLASSIFICATION

CROSS-REFERENCE TO PRIOR APPLICATIONS

This application is the U.S. National Phase application under 35 U.S.C. § 371 of International Application No. PCT/EP2020/086320, filed on Dec. 18, 2020, which claims the benefit of U.S. Provisional Application Ser. No. 62/949,836, filed on Dec. 18, 2019. These applications are hereby incorporated by reference herein.

TECHNICAL FIELD

Various exemplary embodiments disclosed herein relate generally to a co-training framework to mutually improve concept extraction from clinical notes and medical image classification.

BACKGROUND

Various types of clinical tests (e.g., X-ray, MRI, ultrasound) generate both image and text data. These tests are often imaging tests, and the results are documented in reports and/or notes written by skilled professionals (e.g., radiologists) where they describe various observations and findings from the tests. The notes/reports contain different medical concepts (e.g., disease, symptom, anatomy, severity) that need to be identified and extracted so that they can be used for other downstream applications such as AI-enabled clinical diagnosis support, patient status visualization on information dashboards, etc. Traditional natural language processing-based information extraction systems primarily work on the text of the reports/notes, and do not take advantage of the accompanying images. Similarly, medical image classification algorithms primarily rely on image features and do not utilize the accompanying text when they may be available.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a system for training a text report identification machine learning model and an image identification machine learning model, including: a memory; a processor connected to the memory, the processor configured to: initially train a text report machine learning model, using a labeled set of text reports including text pre-processing the text report and extracting features from the pre-processed text report, wherein the extracted features are input into the text report machine learning model; initially train an image machine learning model, using a labeled set of images; apply the initially trained text report machine learning model to a first set of unlabeled text reports with associated images to label the associated images; select a first portion of labeled associated images; re-train the image machine learning model using the selected first portion of labeled associated images; apply the initially trained image machine learning model to a first set of unlabeled images with associated text reports to label the associated text reports; select a first portion of labeled associated text reports; and re-train the text report machine learning model using the selected first portion of labeled associated text reports.

Various embodiments are described, wherein selecting a portion of labeled associated images includes selecting associated images with text report machine learning model outputs having a confidence level above a first confidence threshold, and selecting a portion of labeled associated text reports includes selecting associated text reports with image machine learning model outputs having a confidence level above a second confidence threshold.

Various embodiments are described, wherein selecting a portion of labeled associated images further includes selecting the N associated images with text report machine learning model outputs having the highest confidence levels, wherein N is a predetermined value, and selecting a portion of labeled associated text reports further includes selecting the M associated text reports with image machine learning model outputs having the highest confidence levels, wherein M is a predetermined value.

Various embodiments are described, selecting a portion of labeled associated images includes selecting associated images with text report machine learning model outputs having a confidence level above a first confidence threshold, when there are more than N selected associated images, further selecting N associated images with text reports that have the highest confidence levels, selecting a portion of labeled associated text reports includes selecting associated text reports with image machine learning model outputs having a confidence level above a second confidence threshold, and when there are more than M selected associated text reports, further selecting M associated text reports with image that have the highest confidence levels.

Various embodiments are described, wherein the outputs of the text report machine learning model and image machine learning model indicated the same set of classification concepts.

Various embodiments are described, wherein the image machine learning model is re-trained until the initially trained text report machine learning model is applied to all the unlabeled text reports with associated images, and the text report machine learning model is re-trained until the initially trained image machine learning model is applied to all the unlabeled images with associated text reports.

Various embodiments are described, wherein the image machine learning model is re-trained until the image machine learning model performance on validation set of input image data does not improve, and the text report machine learning model is re-trained until the text report machine learning model performance on a validation set of input text report data does not improve.

Various embodiments are described, wherein the processor is further configured to: apply the retrained text report machine learning model to a second set of unlabeled text reports with associated images to label the associated images; select a second portion of labeled associated images; re-train the retrained image machine learning model using the selected second portion of labeled associated images; apply the retrained image machine learning model to a second set of unlabeled images with associated text reports to label the associated text reports; select a second portion of labeled associated text reports; and re-train the retrained text report machine learning model using the selected second portion of labeled associated text reports.

Further various embodiments relate to a method for training a text report identification machine learning model and an image identification machine learning model, including: initially training a text report machine learning model, using a labeled set of text reports including text pre-processing the text report and extracting features from the pre-processed text report, wherein the extracted features are input into the text report machine learning model; initially training an image machine learning model, using a labeled set of images; applying the initially trained text report machine learning model to a first set of unlabeled text reports with associated images to label the associated images; selecting a first portion of labeled associated images; re-training the image machine learning model using the selected first portion of labeled associated images; applying the initially trained image machine learning model to a first set of unlabeled images with associated text reports to label the associated text reports; selecting a first portion of labeled associated text reports; and re-training the text report machine learning model using the selected first portion of labeled associated text reports.

Various embodiments are described, wherein selecting a portion of labeled associated images includes selecting associated images with text report machine learning model outputs having a confidence level above a first confidence threshold, and selecting a portion of labeled associated text reports includes selecting associated text reports with image machine learning model outputs having a confidence level above a second confidence threshold.

Various embodiments are described, wherein selecting a portion of labeled associated images further includes selecting the N associated images with text report machine learning model outputs having the highest confidence levels, and selecting a portion of labeled associated text reports further includes selecting the M associated text reports with image machine learning model outputs having the highest confidence levels.

Various embodiments are described, wherein selecting a portion of labeled associated images includes selecting associated images with text report machine learning model outputs having a confidence level above a first confidence threshold, when there are more than N selected associated images, further selecting N associated images with text reports that have the highest confidence levels, selecting a portion of labeled associated text reports includes selecting associated text reports with image machine learning model outputs having a confidence level above a second confidence threshold, and when there are more than M selected associated text reports, further selecting M associated text reports with image that have the highest confidence levels.

Various embodiments are described, wherein the outputs of the text report machine learning model and image machine learning model indicated the same set of classification concepts.

Various embodiments are described, wherein the image machine learning model is re-trained until the initially trained text report machine learning model is applied to all the unlabeled text reports with associated images, and the text report machine learning model is re-trained until the initially trained image machine learning model is applied to all the unlabeled images with associated text reports.

Various embodiments are described, wherein the image machine learning model is re-trained until the image machine learning model performance on validation set of input image data does not improve, and the text report machine learning model is re-trained until the text report machine learning model performance on a validation set of input text report data does not improve.

Various embodiments are described, further including: applying the retrained text report machine learning model to a second set of unlabeled text reports with associated images to label the associated images; selecting a second portion of labeled associated images; re-training the retrained image machine learning model using the selected second portion of labeled associated images; applying the retrained image machine learning model to a second set of unlabeled images with associated text reports to label the associated text reports; selecting a second portion of labeled associated text reports; and re-training the retrained text report machine learning model using the selected second portion of labeled associated text reports.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Embodiments of a co-training system will be described herein that implement a co-training framework where an image-based classifier and a text-based classifier mutually generate supplemental training instances for each other in an iterative semi-supervised learning paradigm to gradually improve their individual performances.

Iterative semi-supervised learning increases an initial small collection of labeled training data with supplemental training data that are automatically labeled from a large collection of unlabeled data. However, a text-based learning algorithm that completely relies on text data stays limited to what it can already learn from the text data, and the additionally iterative incremental training data may suffer from monotonicity and lack feature diversity which are important for continued learning. Similar limitations will be faced by an image-based classification algorithm as it will only rely on image features, but could benefit from additional text data which may offer complementary or redundant information. The embodiment of a co-training framework will address this problem by individually training text-based and image-based classifiers with text-based and image-based data that each identify new instances from unlabeled data to generate supplemental training instances for the other, thus allowing each classifier to improve over time as the labeled training data expands in each iteration.

Figure 1:
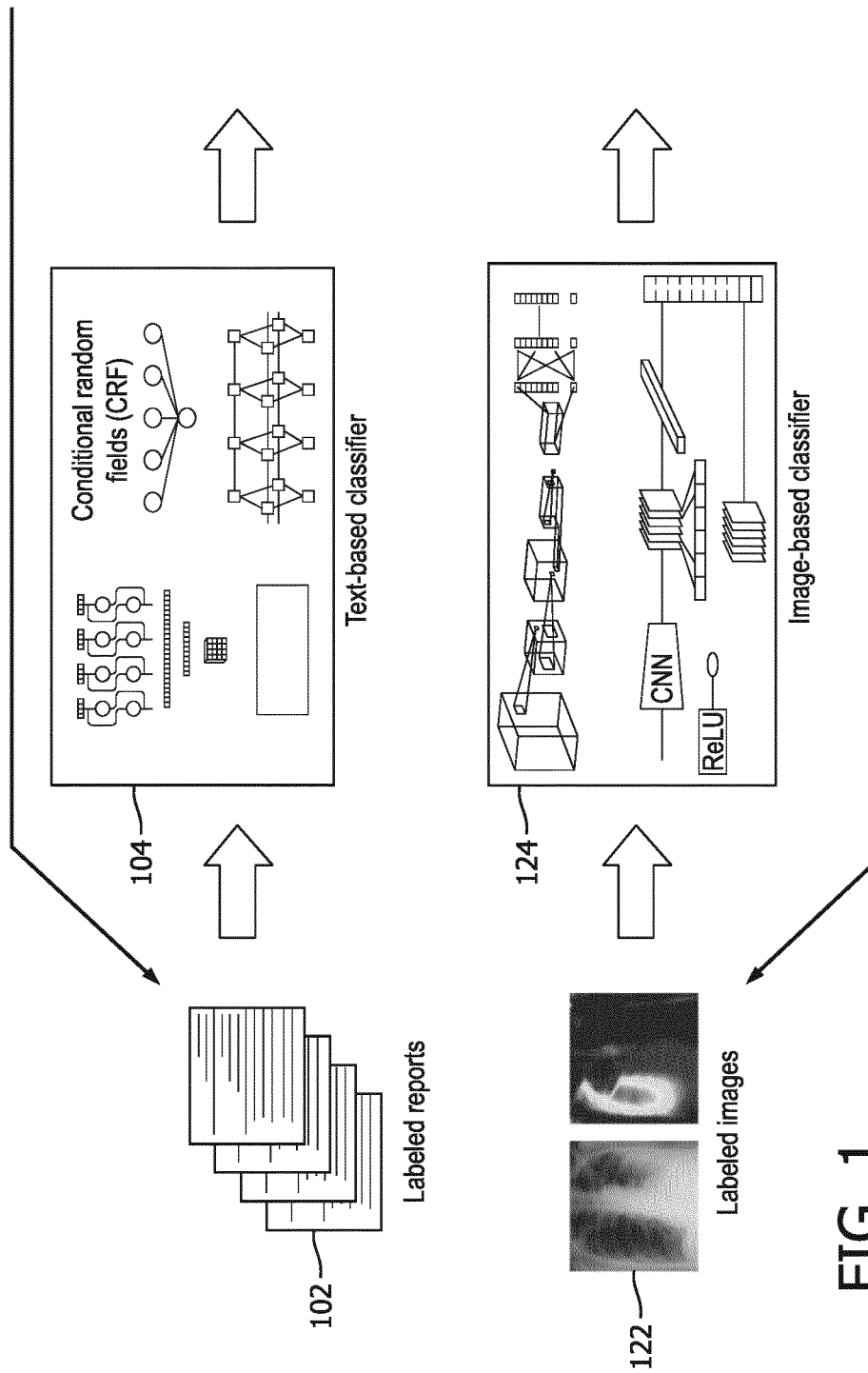
FIG. 1 illustrates a co-training system that leverages two views of the data—a text view and an image view.
Figure 1:
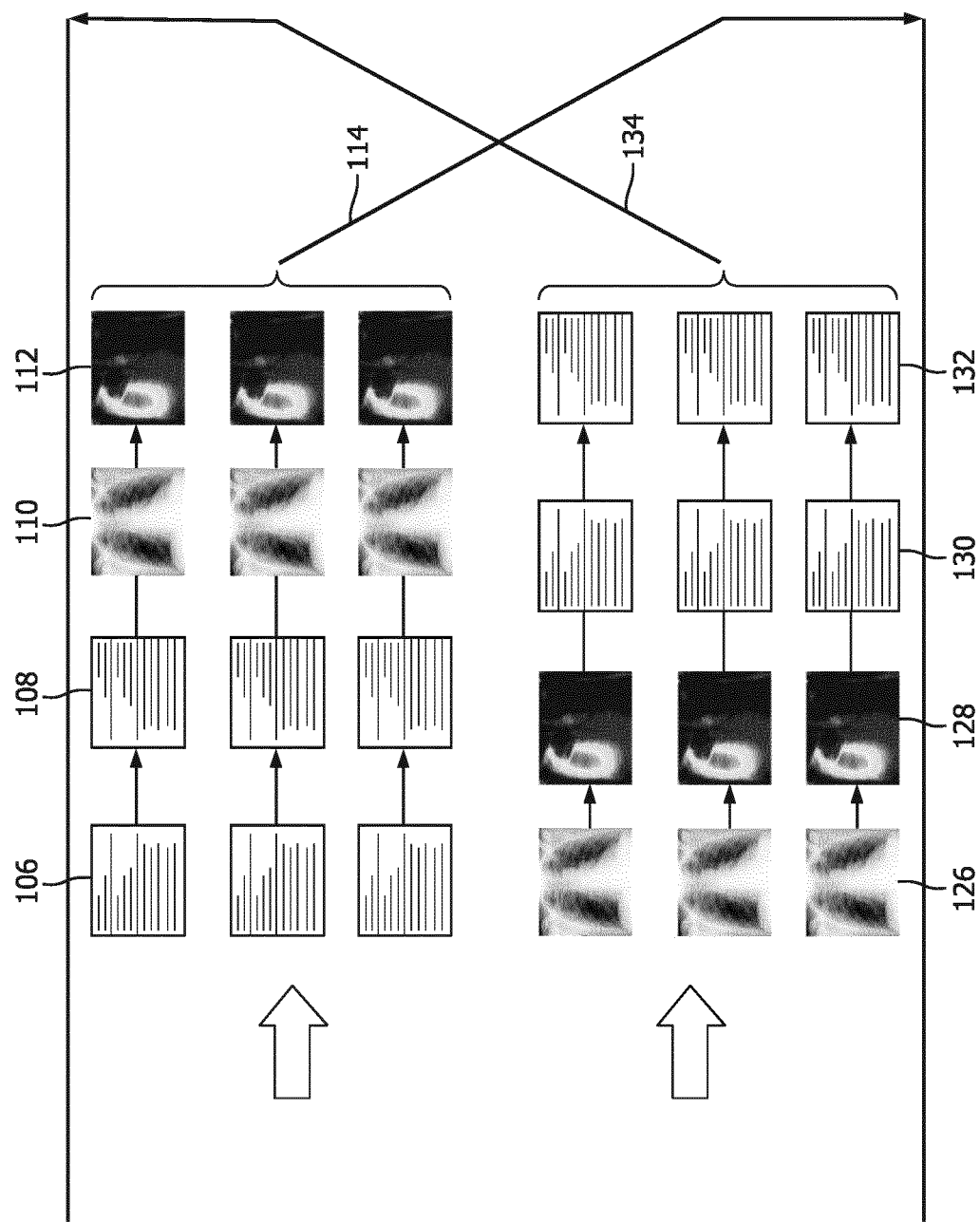

FIG. 1 illustrates a co-training system that leverages two views of the data—(1) a text view, and (2) an image view. First, a text-based concept identification model 104 is trained using labeled reports 102 associated with images. The text identification model 104 may be a text classifier that uses various textual data features and a machine learning algorithm suitable for sequence labeling. Example machine learning algorithms may include conditional random field (CRF) classifier, bidirectional long short-term memory (BiLSTM) networks, BiLSTM-CRF, etc. A small collection of initial labeled training data 102 is used to train the text identification model 104.

Unlabeled text reports 106 are input into the text identification model 104 to generate labeled reports 108. The unlabeled images 110 associated with the unlabeled reports 108 are then labeled using the labels from the labeled reports 108 produced by the text identification model 104. The text identification model 104 may produce a confidence value associated with its labeled outputs. These labeled images 112 may then be used as further training samples for an image identification model 124. Not all of the labeled images 112 may be used as further training samples. In one embodiment, only labeled images 112 associated with labeled reports 108 that have a confidence level above a specified threshold value may be used to further train the image identification model 124. In another embodiment, the number of further training samples may be limited to a threshold number N of training samples, by selecting the N samples with the highest confidence levels. In yet another embodiment if there are more than N samples that exceed the threshold value, only the N values with the highest confidence values may be selected as the training samples. Other methods of limiting the further training samples may be used to ensure that the further training samples are of high enough quality to improve the training of the image identification model 124. These selected training samples may then be sent 114 to further train the image identification model 124.

Figure 2:
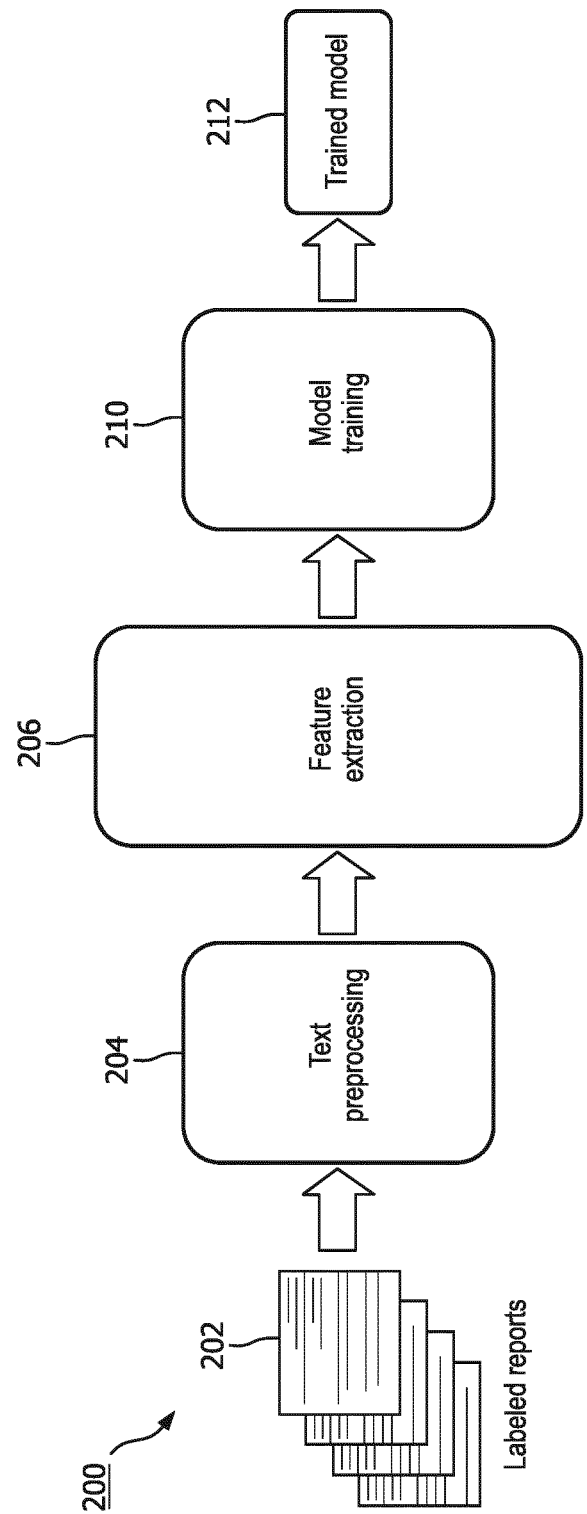
FIG. 2 shows a flow diagram illustrating the training of the text identification model.

FIG. 2 shows a flow diagram illustrating the training 200 of the text identification model 104. The labeled reports 202 first undergo text preprocessing 204. The text pre-processing 204 may include tokenization, lemmatization, case normalization, stopwords removal processing, etc. This text pre-processing 204 takes in the raw text of the labeled reports and processes them into a consistent format in order to facilitate feature extraction. Next, the preprocessed text undergoes feature extraction 206. Feature extraction may include looking at each current word in the context of prior words and next words. Also, context words may be identified. Various types of features may be extracted including morphological, orthographic, lexical, and syntactic features. The feature extraction is used to provide inputs into the text identification model 212. Such features need to be defined in a consistent matter so that model may be trained to generate a consistent known set of extracted concepts out of the text identification model 212.

The table below gives examples of feature names, followed by example text, and the resulting feature value. For example, the first four entries use the example text of Cardiomegaly with the following feature names: Word/Phrase, Lowercase, 1 Character suffix, and 2 Character suffix. The associated values are: Cardiomegaly, cardiomegaly, y, and ly. Many other text feature examples are further demonstrated.

| Feature Name | Example Text | Feature Value |
| --- | --- | --- |
| Word/Phrase | Cardiomegaly | Cardiomegaly |
| Lowercase | Cardiomegaly | Cardiomegaly |
| 1 Character suffix | Cardiomegaly | Y |
| 2 Character suffix | Cardiomegaly | ly |
| If text is uppercase | SVC | True |
| If text is title | Superior Vena Cava | True |
| If text is a digit | 4 | True |
| Lemma form | Increased, increasing, increases | increase |
| Coarse-grained position of speech (POS) | Increased | VERB |
| Fine-grained POS | Increased | VBN (Verb, past participle) |
| Syntactic relation | shift of the trachea | ROOT prep det pobj |
| Syntactic parent | shift of the trachea | shift shift trachea of |
| Orthographic shape | 77F, 2.2 cm | ddX, d.d xx |
| If text is alphabetic | Cardiomegaly, 77F | True, False |
| If text is a stop word | shift of the trachea | False True True False |
| Left edge | shift of the trachea | shift of the the |
| Right edge | shift of the trachea | trachea trachea the trachea |
| If text is a punctuation | ? | True |
| If text starts sentence | Sternal wires are unremarkable. | True False False False False |

Once the features have been extracted for each of the labeled reports 202, these are used to train 210 the machine learning model to produce the text identification model 212. This may correspond to the generating the text identification model 104 using labeled reports 104 of FIG. 1.

Figure 3:
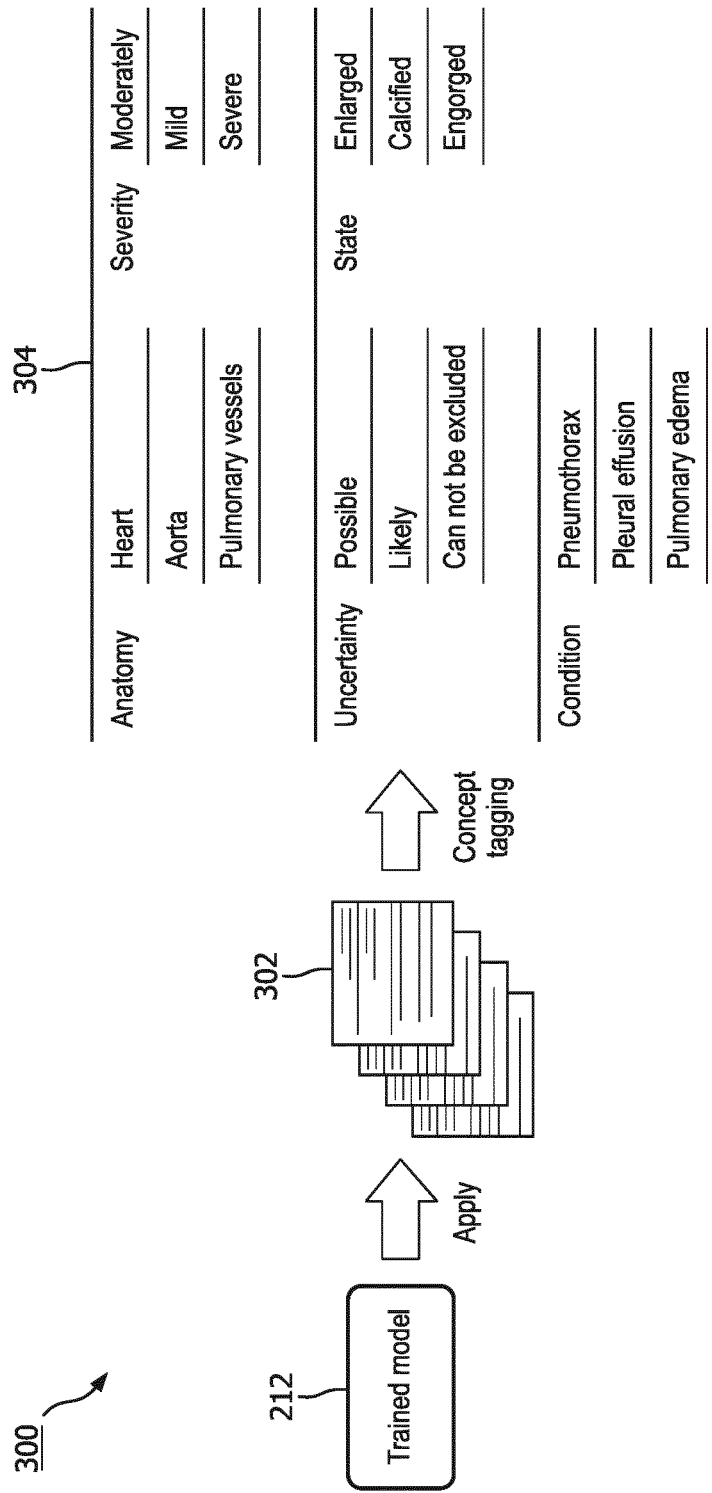
FIG. 3 illustrates the use of the trained text identification model on a set of input unlabeled text reports to produce a set of labels based upon a set of extracted concepts.

FIG. 3 illustrates the use of the trained text identification model 212 on a set of input unlabeled text reports to produce a set of labels based upon a set of extracted concepts 304. This may correspond to steps 106 and 108 from FIG. 1. In this example, a large number of unlabeled text reports 302 may be input into the text identification model 212 to produce outputs of concepts identified in the unlabeled reports 302. These are the concepts that may be used to label the associated unlabeled images 110 to produce labeled images 112.

Next, an image-based concept identification model 124 will be trained using labeled images 122 associated with text reports. The image identification model 124 may be an image classifier that uses various image features and a machine learning algorithm suitable for image processing. An example machine learning algorithm may include convolutional neural networks-based (CNN) class activation mapping model, but other image classifying models may be used. A small collection of initial labeled training data 122 is used to train the image identification model 124.

Unlabeled images 126 are input into the image identification model 124 to generate labeled images 128. The unlabeled text reports 130 associated with the unlabeled images 126 are then labeled using the labels from the labeled images 128 produced by the image identification model 124. The image identification model 124 may produce a confidence value associated with its labeled outputs. The documents associated with these labeled images 132 may then be used as further training samples for the text identification model 104. Not all of the labeled reports 132 may be used as further training samples. In one embodiment, only labeled reports 132 associated with labeled images 128 that have a confidence level above a specified threshold value may be used to further train the text identification model 104. In another embodiment, the number of further training samples may be limited to a threshold number M of training samples, by selecting the M samples with the highest confidence levels. In yet another embodiment if there are more than M samples that exceed the threshold value, only the M values with the highest confidence values may be selected as the training samples. Other methods of limiting the further training samples may be used to ensure that the further training samples are of high enough quality to improve the training of the report identification model 104. These selected training samples may then be sent 134 to further train the text identification model 104.

Figure 4:
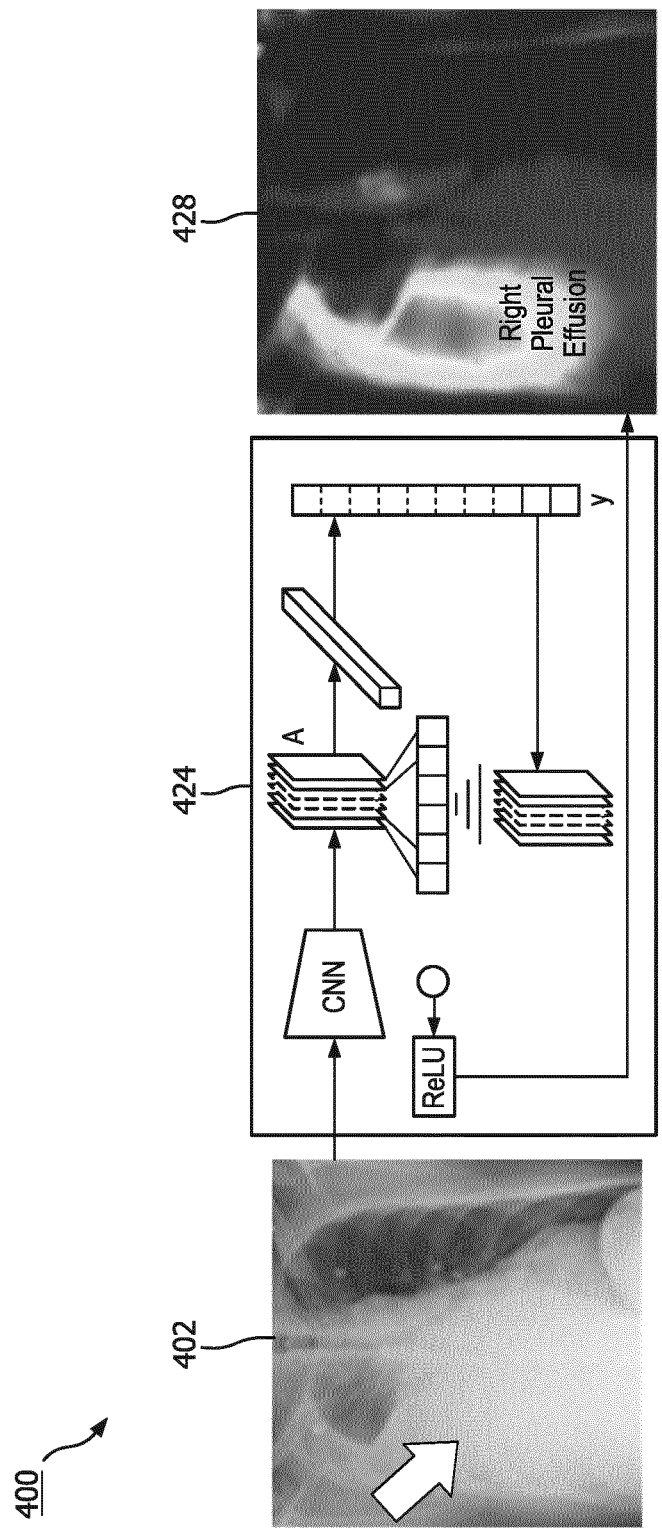
FIG. 4 shows a flow diagram illustrating the image identification model.

FIG. 4 shows a flow diagram 400 illustrating the image identification model 424. The unlabeled images 426 are input into the image identification model 424. The image identification model 424 corresponds to the image identification model 124 in FIG. 1. The image identification model 424 may include a CNN applied to the image to extract features from the unlabeled input images 426. The CNN may employ various layers including convolution layers and pooling layers in various configurations along with the application of rectified linear units (ReLU). Other types of layers may also be used in various configurations. Then the extracted features are input into classification layers to identify various concepts associated with the image. The classification layers may be fully connected layers that flatten the data and then use a softmax layer to produce outputs 428 indicating the presence of the concepts found in the image. The concepts output from the image identification model 424 are consistent with the concepts output from the text identification model. The image identification model 424 may be trained with a small set of initial labeled images as previously described and this initial training is supplemented with selected outputs 114 from applying the text identification model 104 on unlabeled text reports 106.

The features classified by the two models need to be defined in a consistent matter so that models may be trained to generate a consistent known set of extracted concepts out of the two models.

As a result, both trained models 104, 124 will be individually applied to unlabeled data that has clinical reports and their accompanying images paired with each other. The text identification model 104 will be applied to the unstructured text reports to identify a predefined set of medical concepts in the notes in the associated text reports, which will then be used to label the associated unlabeled images. The image identification based model 124 will be applied to unlabeled images to identify a set of medical concepts in the images which will then be used to label the associated unlabeled text reports.

The text reports with identified medical concepts and their corresponding images 114 will be used to supplement the training data 122 of the image identification model 124 to increase its training data for re-training the image identification model 124. The images with identified medical concepts and their corresponding text reports 134 will be used to supplement the training data 102 of the text identification model to increase its training data for re-training the text identification model 104.

The above steps will be repeated until no new reports or images can be identified from the unlabeled data to supplement the labeled training data or concept extraction results starts to degrade as tested on a validation data set.

In another embodiment, first portion of the unlabeled text reports and images may be used to cross train the machine learning models. Then a second portion of the unlabeled text reports and images may be used to cross train the machine learning models. This process is repeated until no new reports or images can be identified from the unlabeled data to supplement the labeled training data or concept extraction results starts to degrade as tested on a validation data set.

The embodiments of the co-training system described herein have various benefits. The co-training system leverages text modality of data in text reports associated with images to improve an image-based classifier to classify test images for concepts and identify a target set of concepts in the images. The co-training system further leverages image modality of data in images associated with text reports to improve a text-based classifier for information extraction from clinical reports. The co-training system also utilizes information from unlabeled clinical test images and reports which is a limitation of supervised learning systems. The co-training system further expands the initial labeled training data in iterations for both image-based and text-based models by incorporating image and text data views in co-training where the data modalities are associated but not overlapping. Finally, the co-training system leverages multimodal data associated with clinical tests to improve computational models in each modality.

While the co-training system is described herein using medical images, such as X-ray, MRI, ultrasound, etc., and their associated medical reports, other images with associated text descriptions may be included. Such examples could be images and associated text found in catalogs, instruction and installations manuals, books, product web sites, social media web sites, news web sites, etc. The co-training system described herein may be used to co-train a text identification and image identification models for use in classifying images and text reports in such situations. As described above, a small set of labeled information may be used to initially train the models, which training can then be supplemented using the co-training system to expand the training data from unlabeled data that includes both an image and associated text. This leads to be better and more robust text identification and image identification models when only a small labeled training set is available.

Figure 5:
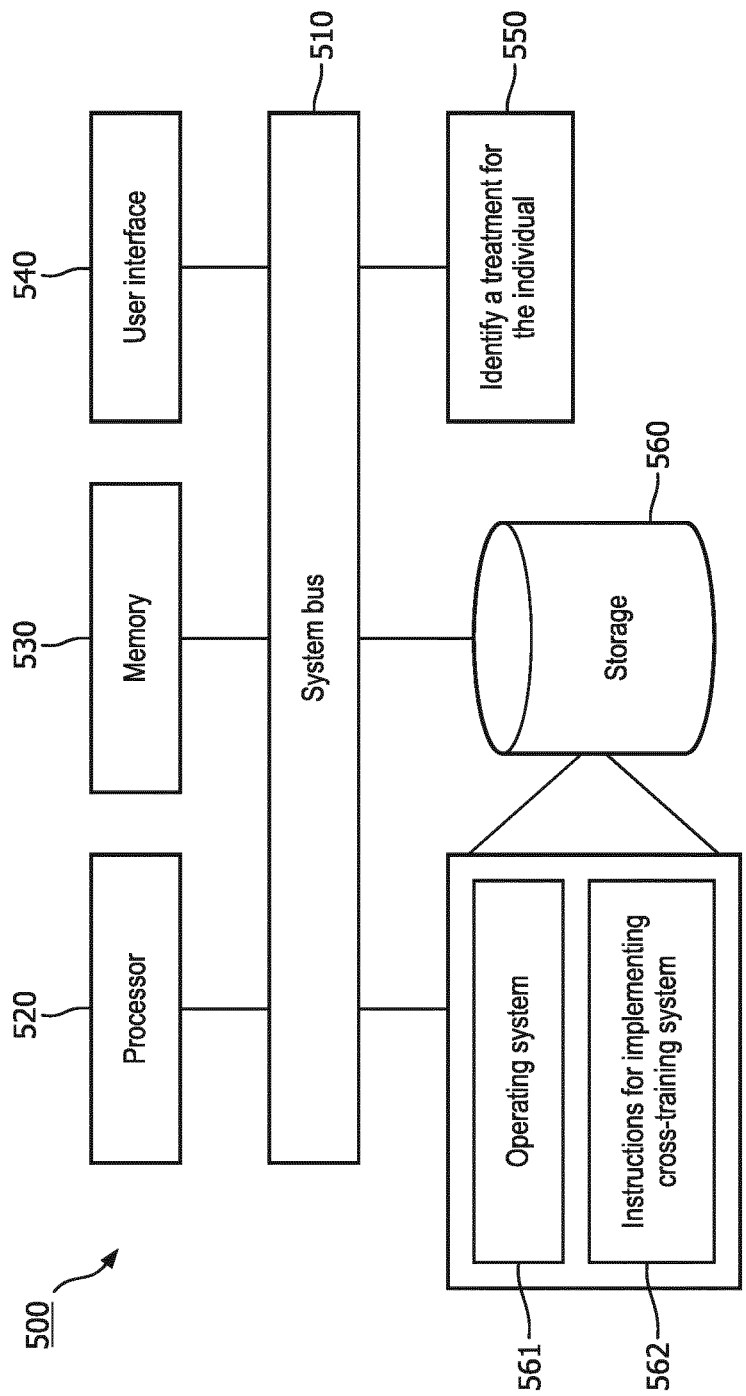
FIG. 5 illustrates an exemplary hardware diagram for implementing co-training system.

FIG. 5 illustrates an exemplary hardware diagram 500 for implementing co-training system. As shown, the device 500 includes a processor 520, memory 530, user interface 540, network interface 550, and storage 560 interconnected via one or more system buses 510. It will be understood that FIG. 5 constitutes, in some respects, an abstraction and that the actual organization of the components of the device 500 may be more complex than illustrated.

The processor 520 may be any hardware device capable of executing instructions stored in memory 530 or storage 560 or otherwise processing data. As such, the processor may include a microprocessor, a graphics processing unit (GPU), field programmable gate array (FPGA), application-specific integrated circuit (ASIC), any processor capable of parallel computing, or other similar devices.

The memory 530 may include various memories such as, for example L1, L2, or L3 cache or system memory. As such, the memory 530 may include static random-access memory (SRAM), dynamic RAM (DRAM), flash memory, read only memory (ROM), or other similar memory devices.

The user interface 540 may include one or more devices for enabling communication with a user and may present information such. For example, the user interface 540 may include a display, a touch interface, a mouse, and/or a keyboard for receiving user commands. In some embodiments, the user interface 540 may include a command line interface or graphical user interface that may be presented to a remote terminal via the network interface 550.

The network interface 550 may include one or more devices for enabling communication with other hardware devices. For example, the network interface 550 may include a network interface card (NIC) configured to communicate according to the Ethernet protocol or other communications protocols, including wireless protocols. Additionally, the network interface 550 may implement a TCP/IP stack for communication according to the TCP/IP protocols. Various alternative or additional hardware or configurations for the network interface 550 will be apparent.

The storage 560 may include one or more machine-readable storage media such as read-only memory (ROM), random-access memory (RAM), magnetic disk storage media, optical storage media, flash-memory devices, or similar storage media. In various embodiments, the storage 560 may store instructions for execution by the processor 520 or data upon with the processor 520 may operate. For example, the storage 560 may store a base operating system 561 for controlling various basic operations of the hardware 500. The storage 562 may store instructions for implementing the co-training system described above including training the machine learning models and running the machine learning models on data to classify.

It will be apparent that various information described as stored in the storage 560 may be additionally or alternatively stored in the memory 530. In this respect, the memory 530 may also be considered to constitute a "storage device" and the storage 560 may be considered a "memory." Various other arrangements will be apparent. Further, the memory 530 and storage 560 may both be considered to be "non-transitory machine-readable media." As used herein, the term "non-transitory" will be understood to exclude transitory signals but to include all forms of storage, including both volatile and non-volatile memories.

While the host device 500 is shown as including one of each described component, the various components may be duplicated in various embodiments. For example, the processor 520 may include multiple microprocessors that are configured to independently execute the methods described herein or are configured to perform steps or subroutines of the methods described herein such that the multiple processors cooperate to achieve the functionality described herein. Such plurality of processors may be of the same or different types. Further, where the device 500 is implemented in a cloud computing system, the various hardware components may belong to separate physical systems. For example, the processor 520 may include a first processor in a first server and a second processor in a second server.

The co-training system described herein provides many benefits as described above. The co-training system improves the classification of images and associated text, by using a co-training framework that allows for the training of the machine learning models using a small set of labeled training data supplemented by cross training using unlabeled data processed by the machine learning models. This system provides a technical improvement in image and text identification systems.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A system for training a text report identification machine learning model and an image identification machine learning model, comprising:
   a memory;
   a processor connected to the memory, the processor configured to:
      initially train a text report machine learning model, using a labeled set of text reports including text pre-processing the text report and extracting features from the pre-processed text report, wherein the extracted features are input into the text report machine learning model;
      initially train an image machine learning model, using a labeled set of images;
      apply the initially trained text report machine learning model to a first set of unlabeled text reports with associated images to label the associated images;
      select a first portion of labeled associated images;
      re-train the image machine learning model using the selected first portion of labeled associated images;
      apply the initially trained image machine learning model to a first set of unlabeled images with associated text reports to label the associated text reports;
      select a first portion of labeled associated text reports; and
      re-train the text report machine learning model using the selected first portion of labeled associated text reports.

2. The system of 1, wherein
   selecting a portion of labeled associated images includes selecting associated images with text report machine learning model outputs having a confidence level above a first confidence threshold, and
   selecting a portion of labeled associated text reports includes selecting associated text reports with image machine learning model outputs having a confidence level above a second confidence threshold.

3. The system of claim 1, wherein
   selecting a portion of labeled associated images further includes selecting the N associated images with text report machine learning model outputs having the highest confidence levels, wherein N is a predetermined value, and selecting a portion of labeled associated text reports further includes selecting the M associated text reports with image machine learning model outputs having the highest confidence levels, wherein M is a predetermined value.

4. The system of claim 1, wherein
selecting a portion of labeled associated images includes selecting associated images with text report machine learning model outputs having a confidence level above a first confidence threshold,
when there are more than N selected associated images, further selecting N associated images with text reports that have the highest confidence levels,
selecting a portion of labeled associated text reports includes selecting associated text reports with image machine learning model outputs having a confidence level above a second confidence threshold, and
when there are more than M selected associated text reports, further selecting M associated text reports with images that have the highest confidence levels.

5. The system of claim 1, wherein the outputs of the text report machine learning model and image machine learning model indicated the same set of classification concepts.

6. The system of claim 1, wherein
the image machine learning model is re-trained until the initially trained text report machine learning model is applied to all the unlabeled text reports with associated images, and
the text report machine learning model is re-trained until the initially trained image machine learning model is applied to all the unlabeled images with associated text reports.

7. The system of claim 1, wherein
the image machine learning model is re-trained until the image machine learning model performance on validation set of input image data does not improve, or
the text report machine learning model is re-trained until the text report machine learning model performance on a validation set of input text report data does not improve.

8. The system of 1, wherein the processor is further configured to:
apply the retrained text report machine learning model to a second set of unlabeled text reports with associated images to label the associated images;
select a second portion of labeled associated images;
re-train the retrained image machine learning model using the selected second portion of labeled associated images;
apply the retrained image machine learning model to a second set of unlabeled images with associated text reports to label the associated text reports;
select a second portion of labeled associated text reports; and
re-train the retrained text report machine learning model using the selected second portion of labeled associated text reports.

9. A method for training a text report identification machine learning model and an image identification machine learning model, comprising:
initially training a text report machine learning model, using a labeled set of text reports including text pre-processing the text report and extracting features from the pre-processed text report, wherein the extracted features are Input into the text report machine learning model;
initially training an Image machine learning model, using a labeled set of images;
applying the initially trained text report machine learning model to a first set of unlabeled text reports with associated images to label the associated images;
selecting a first portion of labeled associated images;
re-training the image machine learning model using the selected first portion of labeled associated images;
applying the initially trained image machine learning model to a first set of unlabeled images with associated text reports to label the associated text reports;
selecting a first portion of labeled associated text reports; and
re-training the text report machine learning model using the selected first portion of labeled associated text reports.

10. The method of claim 9, further comprising,
selecting a portion of labeled associated images including selecting associated images with text report machine learning model outputs having a confidence level above a first confidence threshold or
selecting a portion of labeled associated text reports including selecting associated text reports with image machine learning model outputs having a confidence level above a second confidence threshold.

11. The system of claim 9, wherein
selecting a portion of labeled associated images further includes selecting the N associated images with text report machine learning model outputs having the highest confidence levels, and
selecting a portion of labeled associated text reports further includes selecting the M associated text reports with image machine learning model outputs having the highest confidence levels.

12. The method of claim 9, wherein
selecting a portion of labeled associated images includes selecting associated images with text report machine learning model outputs having a confidence level above a first confidence threshold,
when there are more than N selected associated images, further selecting N associated Images with text reports that have the highest confidence levels,
selecting a portion of labeled associated text reports includes selecting associated text reports with image machine learning model outputs having a confidence level above a second confidence threshold, and
when there are more than M selected associated text reports, further selecting M associated text reports with images that have the highest confidence levels.

13. The method of claim 9, wherein the outputs of the text report machine learning model and image machine learning model indicated the same set of classification concepts.

14. The method of claim 9, wherein
the image machine learning model is re-trained until the initially trained text report machine learning model is applied to all the unlabeled text reports with associated images, and
the text report machine learning model is re-trained until the initially trained image machine learning model is applied to all the unlabeled images with associated text reports.

15. The method of claim 9, wherein
the image machine learning model is re-trained until the image machine learning model performance on validation set of input image data does not improve, and the text report machine learning model is re-trained until the text report machine learning model performance on a validation set of input text report data does not improve.

16. The method of claim 9, further comprising:
applying the retrained text report machine learning model to a second set of unlabeled text reports with associated images to label the associated images;
selecting a second portion of labeled associated images;
re-training the retrained image machine learning model using the selected second portion of labeled associated images;
applying the retrained image machine learning model to a second set of unlabeled images with associated text reports to label the associated text reports;
selecting a second portion of labeled associated text reports; and
re-training the retrained text report machine learning model using the selected second portion of labeled associated text reports.

17. A non-transitory computer readable medium, comprising instructions executable by a processor to carry out the method of:
initially training a text report machine learning model, using a labeled set of text reports including text pre-processing the text report and extracting features from the pre-processed text report, wherein the extracted features are Input into the text report machine learning model;
initially training an image machine learning model, using a labeled set of images;
applying the initially trained text report machine learning model to a first set of unlabeled text reports with associated images to label the associated images;
selecting a first portion of labeled associated images;
re-training the image machine learning model using the selected first portion of labeled associated images;
applying the initially trained image machine learning model to a first set of unlabeled images with associated text reports to label the associated text reports;
selecting a first portion of labeled associated text reports; and
re-training the text report machine learning model using the selected first portion of labeled associated text reports.

18. The non-transitory computer readable medium of claim 17, wherein
the image machine learning model is re-trained until the image machine learning model performance on validation set of input image data does not improve or the text report machine learning model is re-trained until the text report machine learning model performance on a validation set of input text report data does not improve.

19. The non-transitory computer readable medium of claim 17, further comprising,
selecting a portion of labeled associated images including selecting associated images with text report machine learning model outputs having a confidence level above a first confidence threshold, or
selecting a portion of labeled associated text reports including selecting associated text reports with image machine learning model outputs having a confidence level above a second confidence threshold.

20. The non-transitory computer readable medium of claim 17, wherein the text report machine learning model is one of a conditional random field (CRF) classifier, bidirectional long short-term memory (BILSTM) network, and BILSTM-CRF and the image machine learning model is one of a convolutional neural network (CNN) and class activation mapping model.

* * * * *